United States Patent [19]

Tinnell

[11] 4,381,296

[45] * Apr. 26, 1983

[54] TREATMENT FOR HERPES VIRUS

[76] Inventor: James E. Tinnell, 3121 S. Maryland Parkway, Las Vegas, Nev. 89109

[*] Notice: The portion of the term of this patent subsequent to Aug. 25, 1998, has been disclaimed.

[21] Appl. No.: 278,837

[22] Filed: Jun. 29, 1981

Related U.S. Application Data

[63] Continuation-in-part of Ser. No. 162,252, Jun. 23, 1980, Pat. No. 4,285,934, which is a continuation-in-part of Ser. No. 57,453, Jul. 13, 1979, abandoned, which is a continuation-in-part of Ser. No. 879,085, Feb. 21, 1978, abandoned.

[51] Int. Cl.³ ..................... A61K 33/22; A61K 35/78; A61K 31/60

[52] U.S. Cl. .................................. 424/148; 424/195; 424/230

[58] Field of Search ........................ 424/148, 195, 230

[56] References Cited

FOREIGN PATENT DOCUMENTS 880282 9/1971 Canada ................................ 424/148

OTHER PUBLICATIONS

PDR, 27 Ed., 1973, p. 699.

Primary Examiner—Jerome D. Goldberg
Attorney, Agent, or Firm—William H. Drummond

[57] ABSTRACT

A treatment for herpes virus infections topical application of a suspension of tannic acid, and salicyclic acid, preferably in an ethanol solvent/carrier. After treatment, herpes lesions disappear within 4–5 days.

2 Claims, No Drawings

TREATMENT FOR HERPES VIRUS

REFERENCE TO PRIOR APPLICATIONS

The application is a continuation-in-part of application Ser. No. 162,252, filed June 23, 1980 now issued U.S. Pat. No. 4,285,934, which in turn is a continuation-in-part of application Ser. No. 057,453, filed July 13, 1979, which in turn was a continuation-in-part of application Ser. No. 879,085, filed Feb. 21, 1978, both entitled Treatment For Herpes Virus, both now abandoned.

BACKGROUND OF THE INVENTION

Herpes viruses, particularly the herpes simplex virus, are one of the most common and persistent problems faced by the medical profession. It has been estimated that 75% of the population has been infected with herpes simplex virus; while most cases are asymtomatic, chronic outbreaks and orofacial and genital lesions are very common. Herpes genitalis is the second most common venereal disease, with over 100,000 occurrences in the U.S. each year. Orofacial lesions, often referred to as "fever blisters" or "cold sores" are extremely common. The lesions start out as an area of irritation, which develops a vesicle within a few hours. These vesicles generally break, causing secondary infection and spreading to surrounding skin or mucuous membranes, leaving an ulcerated area which scabs and heals from normal immune reactions in about 10–14 days.

After initial infection, the host develops antibodies which may eventually drive the virus into a latent state. The virus may be reactivated by a variety of factors, including ultraviolet rays, fever, stress, fatigue, and trauma. Despite the presence of antibodies, local eruptions recur indiscriminately, and run a generally predictable 10–14 day healing course.

In addition to abundant "folk medicine" cures which abound due to the common nature of the disease, the medical literature is replete with information related to the etiology, analysis, and treatment of herpes viruses. A good summary of the manifestations and treatments for herpes viruses is found in an article in the September, 1976 issue of "Drug Therapy," p. 27, by Michael W. Rytel, M.D., entitled "Herpes Simplex Infections."

The only drug which has been found to be effective in treating herpes simplex is idoxuridine eye drops for herpes keratitis. This drug has not proved successful however, in topical treatments for facial and labial herpes. Recent excitement in the medical community with regard to the efficacy of the topical application of a heterocyclic dye, followed by exposure to incandescent light, has abated due to subsequent testing showing ineffectiveness and cancer-causing potential. Initial successes with cytarbine have also proved illusory.

Most approaches to relieving the effect of herpes viruses have involved topical application of various drugs. Successful topical therapy would be expected to interrupt viral replication in the lesions and promote heating, but would not effect latent viruses. Nevertheless, no systemic cure is known.

No prior use of combinations of boric acid, tannic acid, and salicylic acid for herpes virus treatment is known to applicant. A solution believed to contain borotannic complex, salicylic acid, ethylacetate, benzyl p-hydroxybenzoate, methyl salicylate, and acetic acid in ethanol was marketed under the name "Onycho-Phytex" by Unimed, Inc., for treatment of onychomycosis, which is a fungus which attacks nails of the fingers and toes. The borotannic complex is believed to have been produced by the process described in U.S. Pat. No. 2,970,032, and was present in the amount of about 8% wt (about 5% wt tannic, 3% wt boric); the salicylic acid is believed to have been present in the amount of about 0.7% wt.

In the patent literature, the use of various chemicals, including components of the treatment of the invention, is described for skin eruptions. As early as 1872, Bergengren, U.S. 124,-60, described a skin potion fabricated from boric acid, potassium chlorate, and citric acid, in addition to some flowers and spices.

The use of an alcohol-glycerine solution of salicylic acid and boric acid for treating local skin diseases caused by vegetable parasites (e.g., ringworm, "athlete's foot") is described in Nichols, U.S. Pat. No. 2,095,571, issued Oct. 12, 1937. Salicylic acid is used in concentrations of 3–10% wt as a fungus inhibitor, and boric acid was added to alleviate itching and to impart antiseptic properties. Prehn, U.S. Pat. No. 2,175,780, issued Oct. 10, 1939, describes a powder comprising salicylic acid, methanol, and champhor, in a powder vehicle of boric acid and starch for topical treatment of fungus and dermatitis.

The use of combinations of boric and tannic acids in skin treatment compositions is also disclosed in the literature. Jekel, U.S. Pat. No. 2,970,032, issued Jan. 31, 1961, discloses the combination of certain tannin/boric acid reaction products in a special solvent which is used for treatment of mycoses. Shelton, U.S. Pat. No. 2,276,241, issued Mar. 10, 1942, describes an aqueous medicinal composition for skin infections comprising an extract of catechol tannin for soothing effect, a phenolic antiseptic compound, and boric acid for pH control.

The literature does not describe any topical treatment which relieves herpes simplex. However, it has not been discovered that a very specific combination of ingredients is highly effective for the topical treatment of herpes viruses.

Accordingly, it is an object of the invention to provide a novel composition for topical treatment of herpes viruses. It is another object of the invention to provide a novel method for treating these viruses. A still further object of the invention is to provide a composition for treating herpes simplex lesions which not only causes the remission of the viruses but also importantly reduces its recurrence.

SUMMARY OF THE INVENTION

A composition for the topic treatment of herpes virus lesions comprises effective amounts of tannic acid, boric acid and salicylic acid in a liquid carrier.

DETAILED DESCRIPTION OF THE INVENTION

According to the invention, I provide a composition for and method of use of such composition, for the topic treatment of herpes virus lesions, which comprises about 2–12% wt tannic acid, 2–12% wt boric acid and about 1–6% wt salicylic acid, with the balance being a suitable liquid carrier such as, for example, ethanol. Within the foregoing ranges, I prefer to employ about 2–7% wt tannic acid, 2–7% wt boric acid and 1–5% wt salicylic acid. Higher concentrations are more effective, but may cause burning or irritation of sensitive mucosa; in particular, concentrations over 8% wt salicylic acid causes burning and discomfort. Therefore, concentrations at the lower end of the preferred range are used for infections of the tongue, buccal or genital mucosa. The compositions of the invention are clear solutions having about 7 to 14% by volume (settled) of solid particles, which are slurried by shaking prior to application.

Treatment is effected by applying a small quantity of the suspension directly to the lesions with a cotton swab, soft brush, or sponge. Any quantity sufficient to cover the lesions with the suspension is effective. Treatments are preferably applied 2 times per day for about three days. With the more concentrated solutions, erythema, pain, and itching cease within four to twelve hours of the first application, and healing occurs in 48-72 hours. In almost all cases, pain is substantially relieved in less than one hour from the first treatment. All lesions clear in 4-5 days with little or no scarring. If treatment begins on the first day when the patient notices the eruption, the infection will generally not reach the vesicular stage, and secondary infection and spreading to surrounding areas will not occur.

Very highh rates of successful remission of herpes virus on the external skin, tongue, buccal mucosa, and genitalia have been obtained with treatment in accordance with the invention. This treatment is not recommended for herpes infections of the eye, since the acidity of the suspension would cause burning of the eye tissues. For reasons not well understood, the treatment of the invention also appears to have a retardant effect on the virus, substantially prolonging the time between recurrences, and in some cases apparently eliminating the virus altogether. I have also discovered that the compositions described above are effective in the treatment of leukoplakia of the mouth and vulva, acne and contact dermatitis.

The particular combination of ingredients of the invention appears to have a synergistic effect in healing the herpes virus, leukoplakia, acne, and contact dermatitis lesions compared to solutions of the ingredients alone or in other combinations. The relative effectiveness is indicated in the following table, which illustrates the effects of treating patients with various types of herpes virus eruptions with ethanol solutions of each composition.

TABLE I

| Composition (% wt) | % of Patients Which Will Be Improved Within 4 Days |
| --- | --- |
| Boric acid (7%) | 20% |
| Salicylic acid (3%) | 10% |
| Boric acid (7%) & Salicylic (3%) | 30% |
| Tannic acid (7%) | 20% |
| Boric acid (7%) & Tannic acid (7%) | 30% |
| Tannic acid (7%) & Salicylic acid (3%) | 30% |
| Boric acid (2%), Tannic acid (2%), & Salicylic acid (1%) | 100% |
| Boric acid (7%) & Tannic acid (7%) & Salicylic acid (3%) | 100% |
| Boric acid (12%), Tannic acid (12%) & Salicylic acid (6%) | 100% |

Solutions having approximately double the concentrations of ingredients of the suspension of the invention used in the above experiments have been found to be most effective for non-mucosal lesions, promoting healing substantially faster. In treating over 200 patients, no known failures occurred. Approximately 25% of these patients did not return for followup observation; while it might be presumed that their absence was indicative of success of the treatment, the data are nonetheless unavailable. Except for the recommendations on component concentrations discussed above, no contraindications have been found.

The solvent/carrier may be any liquid vehicle that does not appreciably react with the components to reduce their efficacy, and which does not irritate the skin. Alcohol, water, or a mixture thereof, are all appropriate vehicles. The alcohol is preferably ethanol, isopropyl alcohol, or methanol; alcohols are preferred because they evaporate quickly and do not adversely affect the skin. Typical solvent/carriers are 70% IPA (aqueous), 95% ethanol, and 50% methanol.

The mixtures of the invention are easily made by weighing proper quantities of the components and adding them singly or together to the liquid base, and shaking the resulting mixture to hasten dissolution of the components. Additional components (e.g., skin softeners) may be used as long as the effectiveness of the solution is not impaired.

The invention is best illustrated with reference to the following examples:

EXAMPLE 1

A 23-year old white female patient was diagnosed as having herpes simplex in the right buttocks and right lower lip and surrounding cheek area. In the lip area she had about 8 to 10 vesicles in an area of erythema 1" in diameter in the lateral portion of the right lower lip. In the buttocks area, 10 lesions were located in a circle approximately 5" in diameter; each lesion contained 6 to 8 vesicles in a 2" area, with surrounding erythema of an additional inch around the vesicles. Formation of the lesions had continued in the circular area for about 1 year, with adjacent new lesions breaking out every week before the old lesions could heal. The patient had tried smallpox injections, ether treatment, and other chemotherapy without success. A suspension of treating solution comprising 15% wt boric acid, 7% wt salicylic acid, and 15% wt tannic acid in an ethanol carrier was applied to all of the lesions. The pain lessened within 12 hours and was totally clear with 18 hours on both the lip and cheek area and the buttocks area. The treatment process was repeated on a daily basis after the first application. On the second day all the lesions appeared to be involuting; the erythema was clearing away and the vesicles were disappearing. By the fourth day the lesions were turning darker and all the vesicles were gone. This was the first time this patient had been without an active lesion in one year. Eleven days after the initial treatment all of the lesions on the buttocks were clearing and the lesion on the lip and cheek were totally gone. Seventeen days after the initial treatment, another small herpes lesion appeared on the lip, and was treated with the same solution. The lesion disappeared in 36 hours after only one treatment.

The patient had a recurrence on the buttocks about 2 months after the first treatment but after 2 days of treatment, the lesion disappeared and all the pain and itching was gone. Another occurrence about 3 months later was treated for 3 days with daily applications of the same solution, and the lesion again disappeared.

EXAMPLE 2

A 28-year old male patient had a herpes simplex lesion on the dorsum of the skin of the penis about ⅔ of the distance between the base of the penis and the glans. The lesion had been recurring about every 6 weeks for about 9 months and involved an area of approximately 5 centimeters containing 6 to 8 vesicles. Each recurrence involved a pain lasting from 4 to 7 days, with surrounding redness and sore area lasting from 12 to 20 days. The solution described in Example 1 was topically applied for 4 days. All pain ceased within 12 hours and the vesicles and redness were clear within 3 days.

EXAMPLE 3

A 24-year old female patient had herpes zoster lesions on the left lower side of her back. The treating solution of Example 1 was applied for 2 consecutive days, with the pain stopping within 12 hours and the vesicles and erythema disappearing in about 2 days. Recurrences about 4 and 7 months after the first treatment were treated with single applications of the same solution, and in each case the lesion cleared within 48 hours.

EXAMPLE 4

A 26-year old female patient had recurrent herpes simplex infections on her right buttocks for 2 years. Lesions had erupted about every 3 to 4 months. Four consecutive daily applications of the treating solution of Example 1 caused elimination of the pain within 12 hours and remission of the redness and vesicles in about 3 days. Several subsequent recurrences were similarly treated and within 3 days, all of the redness, swelling, and lesions had disappeared.

EXAMPLE 5

The patient was a 31-year old male having herpes simplex eruptions approximately every 2 months for 2 years on his penis. The normal course of the infection included about 5 days of extreme soreness, with complete healing in about 2 weeks. With daily applications of the suspension described in Example 1, the lesions were clear in 5 days. Two weeks after healing, several new small vesicles appeared distal to the previous infection. Again, the lesion healed within 5 days. Three subsequent recurrences over a 10 month period were also treated, with the lesions resolving within about 3 days.

EXAMPLE 6

A 33-year old female patient was seen, having a 17-year history of herpes simplex eruptions on the right cheek area after exposure to the sun. The lesions usually involved an area of 7 to 9 centimeters, covering almost the entire right cheek. Three consecutive daily applications of the treatments solution of Example 1 caused remission of all lesions. Subsequent eruptions were similarly treated with identical results.

EXAMPLE 7

A 22-year old male patient was diagnosed as having herpes simplex infection of the lower lip and on the penis. Treating solution as described in Example 1 was applied liberally with cotton tipped swabs daily for 3 days. All erythema had disappeared and the vesicles had cleared by the fourth day. Pain had disappeared in about 12 hours.

EXAMPLE 8

A 20-year old female patient was diagnosed as having herpes infection of the left vulva and on the left side of the rectum. After 1 day of treatment with the solution of Example 1, the pain had lessened and the irritation was disappearing. The lesions were treated for 3 successive days with the solution; by the fifth day after the first treatment, the lesions had disappeared.

EXAMPLE 9

A 59-year old female patient had a herpes simplex infection on her lower lip. The treating solution of Example 1 was applied daily for 3 days. The lesions were totally clear by the fourth day.

EXAMPLE 10

A 34-year old male patient having a history of herpes simplex eruptions of the lip every 4 to 6 weeks for about 2 years was subjected to treatment of the lesions with the solution of Example 1. Daily treatments for 3 days cleared the lesions entirely by the fifth day. A subsequent recurrence was similarly treated with the same results.

EXAMPLE 11

A 32-year old female patient was diagnosed as having herpes simplex kissing lesions of the vulva. Treating solution having 15% wt boric acid, 7% wt salicylic acid, and 15% wt tannic acid in an ethanol carrier was applied daily for 3 days. The lesions cleared within 3 days, and all induration was gone on the fifth day.

EXAMPLE 12

A 24-year old male patient diagnosed as having herpes simplex infection of the glans and on the skin of the shaft of the penis. The treatment solution of Example 1 was liberally applied on the affected skin area each day for 3 days. The pain subsided in about 12 hours, and vesicles disappeared on the third day. All lesions were clearing by the fourth day.

EXAMPLE 13

A 31-year old female patient having herpes simplex infection of the vulva was treated liberally with the solution of Example 1. The pain subsided within 4 hours, and the induration surrounding the lesions was about 50% clear by the second day. Daily treatments were effected for 4 days, and by the fourth day the lesions had entirely cleared.

EXAMPLE 14

A male having herpes simplex infection on the proximal medial aspect of the left forefinger had persistent recurrences every few weeks for about a year. Scarred areas about 1" above the finger on the dorsal of the hand caused by a previous occurrence about 1 month earlier. The lesion was treated daily for 3 days with the solution of Example 1. Pain dissipated in less than 12 hours, and 4 days later the lesions were clearing.

EXAMPLE 15

A 17-year old female having herpes simplex lesions over the entire vulvar area including the labia majora and perineum. The patient was in considerable pain. Treating solution of the invention was applied liberally with cotton swabs to the entire affected area for four days. Pain and erythema lessened with 12 hours of the initial treatment and had almost disappeared after one day. The lesions cleared entirely by the fifth day.

EXAMPLE 16

A 45-year old male having a huge herpes simplex eruption involving the entire mid lower lip, with secondary impetigo of the entire chain, was treated by topical application of Example 1. Herpes lesions began to clear with 24 hours; the secondary infections cleared with administration of antibiotics.

EXAMPLE 17

A 36-year old female patient having a history of chronic herpes simplex eruptions had tried many known remedies without success. Following topical application of Example 1 to an eruption on the right cheek, soreness began to subside within thirty minutes, with substantial improvement after two days. Recurrence several months later was similarly treated, with substantial regression two days after treatment.

EXAMPLE 18

A 13-year old male patient had three herpes lesions. Example 1 was applied four times daily; on the second day, the patient returned with lesions clearing, and pain had disappeared.

EXAMPLE 19

A 38-year old male patient had herpes eruptions on his uppeer legs near the groin area. Itching stopped within an hour of the first application of Example 1; application of the solution four times daily caused remission within a few days.

EXAMPLE 20

A 44-year old female patient had suffered from chronic herpes infections for many years. The infections would start at the corner of her mouth, and she would be unable to open her mouth without severe pain. Subsequently, the eruption frequently would bleed, and would spread to adjacent areas of her lips. Within one-half hour of application of Example 1 to an eruption on her mouth, the pain subsided to the point where she could open her mouth fully. Full healing followed within a few days.

EXAMPLE 21

A 25-year old female patient with chronic herpes visited with a lesion on her lip. Application of Example 1 four times a day caused relief of the soreness and itching within two days.

EXAMPLE 22

A 28-year old female patient with a history of chronic herpes infections which had never resolved before 14 days despite the use of many different treatments visited with herpes lesions on her lip, thigh, and vulva. Pain subsided within 30 minutes, and the lesions all cleared in 2-4 days (application four times per day).

EXAMPLE 23

A 23-year old female patient having a history of lip herpes every several months, or upon exposure to the sun, visited with lip lesions. Application four times a day of Example 1 cleared the lesions completely in 2-4 days, and subsequent recurrences were substantially reduced.

Observation of a large number of cases of herpes simplex infections of various areas of the body indicated that treatment in accordance with the invention predictably causes pain to subside in less than 12 hours (usually less than an hour), followed by clearing of the lesions in 4 to 5 days rather than the normal course of 2 to 3 weeks. It has also been observed that viral shedding to another person through oral or sexual contact ceases after the lesions have been treated for about a 24-48 hour period. In the absence of the treatment of the invention, a patient having genital herpes must refrain from sexual intercourse for three weeks. In addition, it has been observed that patients with persistent recurrences of herpes simplex virus who have undergone several treatments in accordance with the invention appear to develop an immunity from subsequent recurrences. Theoretically it is possible that eradication of peripheral viral inocula might eradicate the central latent virus after a plurality of local treatments.

It has been found that treatment of lesions before rupture of the vesicles will generally avoid the secondary infections that frequently occur after rupture. Secondary infections extend the time of pain for 5-7 days and usually require antibiotic therapy before resolution.

While the invention has been described in detail with respect to specific treatment solutions, it should be realized that certain modifications can be made within the scope and spirit of the invention, which is directed to the 3 acid components of the treatment solution. The addition of other anti-viral components, skin softeners, and the like is contemplated. In addition, changes in the solvent/carrier are also contemplated. Accordingly, the invention should be limited only by the following claims.

I claim:

1. A composition comprising boric acid, tannic acid and salicylic acid in the weight ratios of about 2-12:2-12:1-6.

2. A method for treatment of herpes virus lesions in a human host comprising topically applying to the lesions an effective amount of a composition comprising boric acid, tannic acid and salicylic acid in the weight ratios of about 2-12:2-12:1-6.

* * * * *